United States Patent [19]

Swei et al.

[11] Patent Number: 5,233,067

[45] Date of Patent: Aug. 3, 1993

[54] METALLIZED POLYMERIC SUBSTRATES

[75] Inventors: Gwo Swei, Northborough; Kenneth W. Kristal, Worcester, both of Mass.

[73] Assignee: Rogers Corporation, Rogers, Conn.

[21] Appl. No.: 522,375

[22] Filed: May 8, 1990

[51] Int. Cl.[5] .......................... C07F 7/08; C07F 7/10; C07F 7/18
[52] U.S. Cl. .................... 556/427; 556/413; 556/438; 556/439; 556/440; 556/414; 556/404; 556/405; 556/452; 556/454; 556/457; 556/458; 556/459; 549/215
[58] Field of Search ............ 556/427, 413, 438, 439, 556/440, 414, 404, 405, 452, 454, 457, 458, 459; 542/215

[56] References Cited

U.S. PATENT DOCUMENTS

| | | | |
|---|---|---|---|
| 2,557,803 | 6/1951 | Sommer | 556/425 |
| 4,718,993 | 1/1988 | Caputa et al. | 204/15 |
| 4,812,363 | 3/1989 | Bell et al. | 428/420 |
| 4,981,937 | 1/1991 | Kuriyama et al. | 556/427 X |

FOREIGN PATENT DOCUMENTS 8802412  4/1988  World Int. Prop. O. .

*Primary Examiner*—Paul F. Shaver
*Attorney, Agent, or Firm*—Fishman, Dionne & Cantor

[57] ABSTRACT

A method for metallizing a polymeric substrate is disclosed. The method includes contacting a surface of an etched polymeric substrate with a silane coupling agent and depositing a metallic layer over the surface. The silane coupling agent forms a chemical linkage between the substrate and the metallic layer. A coupling agent composition and a metallized polymeric substrate are also described.

6 Claims, 1 Drawing Sheet

METALLIZED POLYMERIC SUBSTRATES

TECHNICAL FIELD

This invention relates to metallized polymeric substrates and more particularly to coupling agents for use in metallized polymeric substrates.

BACKGROUND OF THE INVENTION

Metal clad polymeric substrates for use in circuit laminates are known. Metallized polymeric laminates may be constructed by melt lamination techniques or by additive processes such as vacuum deposition or electroless deposition.

In each of the conventional methods adhesion between the substrates and metal layer is provided by mechanical interlocking of the metal layer and the surface substrate, i.e., adhesion is a function of substrate surface roughness. In some applications, e.g., high frequency circuits, a smooth metal/polymeric interface is desirable. None of the conventional methods provide a smooth metal/polymeric interface and acceptable adhesion.

Melt lamination techniques suffer from an additional drawback in regard to metallizing high temperature polymeric substrates. The coefficient of thermal expansion mismatch between the substrate and the metal layer results in stress formation within the laminate as the substrate is cooled from the melt to room temperature.

What is needed in the art, particularly in regard to high performance laminates for microwave applications, is a way to overcome the above deficiencies.

DISCLOSURE OF THE INVENTION

A coupling agent for providing improved adhesion between a metallic layer and a polymeric layer of a metallized polymeric substrate is described. The coupling agent has the structural formula:

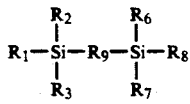

wherein:
$R_1$ is chosen from the group consisting of aminoalkyl, haloalkyl, mercaptoalkyl, carboxyalkyl, glycidoxyalkyl, alkenyl and isocyanatoalkyl.
$R_2$, $R_3$, $R_6$ and $R_7$ are hydrolyzable groups;
$R_8$ is chosen from the group consisting of aminoalkyl, mercaptoalkyl and diphenylphosphinoalkyl.
$R_9$ is oxygen, alkyl, alkylaminoalkyl or alkylthioalkyl.

A process for metallizing a polymeric substrate is disclosed. The process includes etching a surface of the substrate to form reactive groups on the surface, contacting the surface with a coupling agent having the structural formula given above, reacting the $R_1$ group with one of the reactive groups on the surface, and depositing a metallic layer on the surface so that the $R_8$ group reacts with the metallic layer.

An alternative process for metallizing a polymeric substrate is also disclosed. A surface of a polymeric substrate is contacted with an etchant to form reactive groups on the surface. The surface is then contacted with a first organosilane having the structural formula:

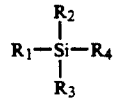

wherein:
$R_1$, $R_2$ and $R_3$ are defined as above; and
$R_4$ is a reactive functional group, a hydrolyzable group or an alkyl group.

The $R_1$ group is reacted with one of the reactive groups on the surface of the substrate. The surface is contacted with a second organosilane having the structural formula:

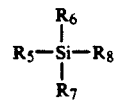

wherein:
$R_5$ is a reactive functional group, a hydrolyzable group or an alkyl group;
$R_6$ and $R_7$ and $R_8$ are defined as above.

The $R_5$ group on the second organosilane is reacted with the $R_4$ group on the first organosilane to form a coupling agent having the structural formula:

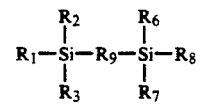

wherein:
$R_1$, $R_2$, $R_3$, $R_6$, $R_7$, $R_8$ and $R_9$ are defined as above.

A metallic layer is deposited on the surface so that the $R_8$ group reacts with the metallic layer.

A composite laminate is also disclosed. The laminate includes a polymeric substrate, a metal layer covering a surface of the substrate, and a coupling agent having the above described structural formula between the substrate and the metal layer.

DETAILED DESCRIPTION OF THE INVENTION

Figure 1:
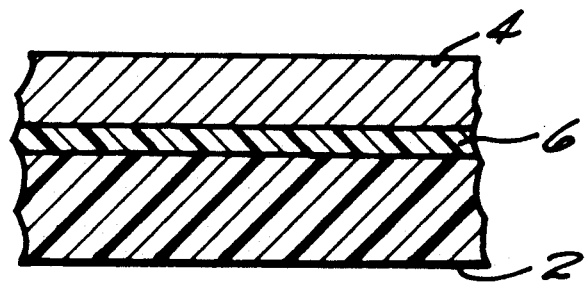
FIG. 1 shows a schematic cross sectional view of a composite laminate of the present invention.

FIG. 1 shows a cross sectional view of a composite laminate of the present invention. The laminate includes a polymeric substrate 2, a metal layer 4 and a layer of coupling agent 6 between the substrate 2 and the metal layer 4.

Figure 2:
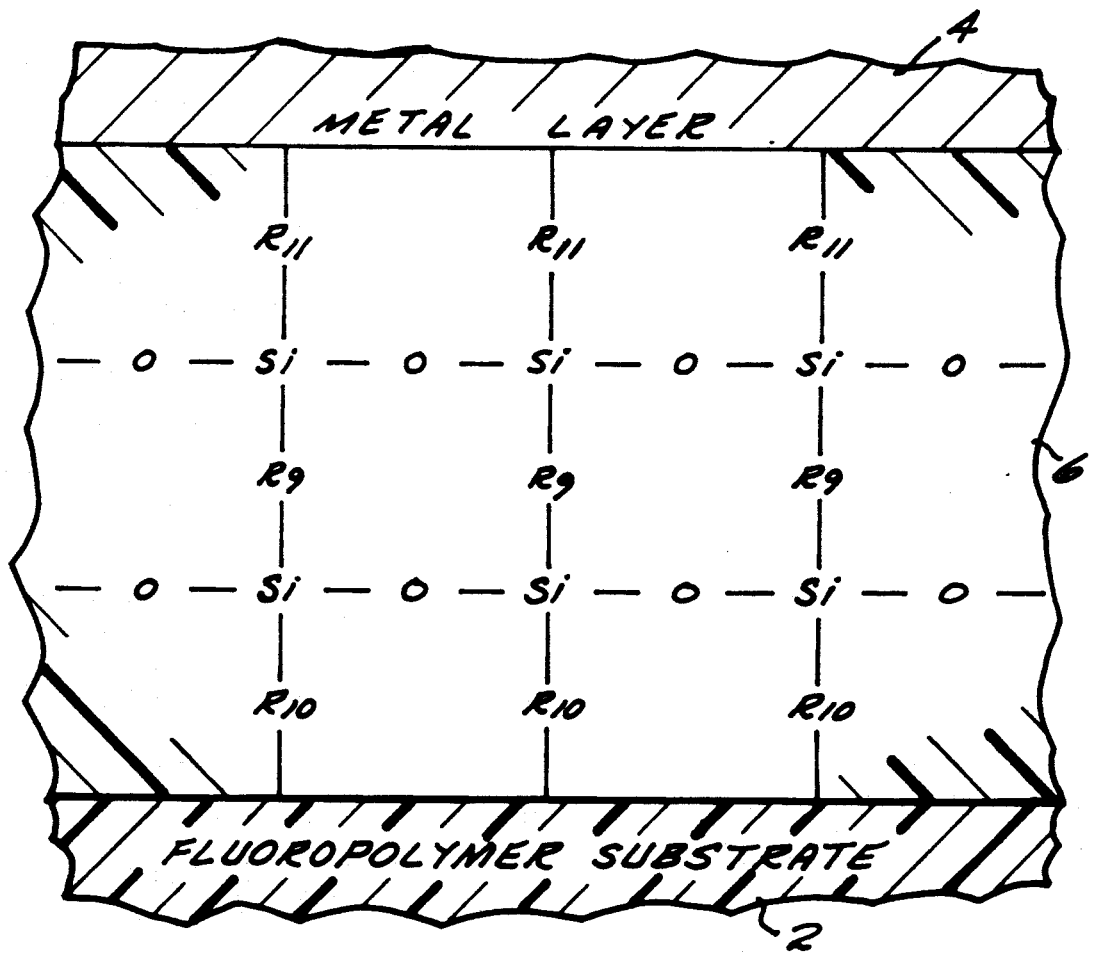
FIG. 2 shows a schematic representation of a cross section of the coupling agent layer of the composite laminate of the present invention.

FIG. 2 shows a schematic representation of the coupling agent layer 6 of the laminate of the present invention. The embodiment shown includes a crosslinked coupling agent layer having a plurality of $R_{10}$ substituent groups which are chemically bonded to the substrate 2 and a plurality of $R_{11}$ substituent groups which are chemically bonded to the metal layer 4. The composition of the coupling agent and of the $R_9$, $R_{10}$ and $R_{11}$ substituent groups are discussed below.

The polymeric substrate of the present invention may comprise any polymeric material. Fluoropolymer substrates and particularly glass or ceramic filled fluoropolymeric composite substrates are preferred. Suitable fluoropolymer substrates include polytetrafluoroethylene (PTFE) and copolymers of tetrafluoroethylene, e.g. tetrafluoroethylene/perfluoropropyl vinyl ether copolymer (FEA), tetrafluoroethylene/hexafluoropropylene copolymer (FEP), polychlorotrifluoroethylene (PCTFE), copolymers of chlorotrifluoroethylene e.g. ethylene/chlorotrifluoroethylene copolymer (ECTFE), and ethylene/tetrafluoroethylene copolymers. Fluoropolymer composite substrates which include a fluoropolymer matrix and up to 65 wt % glass or ceramic particulate filler are particularly preferred substrate materials.

A surface of the polymeric substrate is etched to form reactive groups on the surface. Preferably the substrate is cleaned with a hydrocarbon solvent prior to etching. Any etchant that forms reactive groups on the surface of the polymeric substrate is suitable for the practice of the present invention. Suitable reactive groups that may be formed on the surface of the substrate include unsaturated bonds (e.g. double and triple bonds), hydroxyl groups and carbonyl groups. Sodium naphthalene is the preferred etchant for etching fluoropolymer surfaces. Sodium naphthalene etchants that are suitable for practice of the present invention are commercially available from a number of sources.

The first organosilane includes a functional group that may be reacted with the reactive groups on the surface of the substrate.

Organosilanes which are suitable as the first organosilane of the present invention are those according to the structural formula:

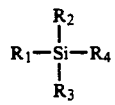

wherein:

$R_1$ is a reactive functional group;
$R_2$ and $R_3$ are hydrolyzable groups; and
$R_4$ is a reactive functional group, a hydrolyzable group or an alkyl group.

Suitable reactive functional groups include aminoaklyl, (e.g. aminopropyl, aminobutyl) groups, haloalkyl, (e.g. chloromethyl, chloropropyl) groups, mercaptoalkyl, (e.g. mercaptoethyl, mercaptopropyl) groups, carboxylalkyl, (e.g. methacryloxypropyl, carboxypropyl) groups, glycidoxyalkyl, (e.g. glycidoxypropyl) groups, alkenyl (e.g. allyl, vinyl) groups, and isocyanotoalkyl (e.g. isocyanatopropyl) groups. Preferably, the reactive functional group comprises an alkenyl, aminoalkyl, glycidoxyalkyl or mercaptoalkyl group. Most preferably, the reactive functional group comprises a vinyl or mercaptoalkyl group.

Suitable hydrolyzable functional groups include alkoxyl (e.g. methoxyl, ethoxyl, butoxyl) groups, acyloxyl groups, hydroxyl groups and halo (e.g. chloro, bromo)- groups. Preferably, the hydrolyzable groups comprise alkoxyl groups. Most preferably, the hydrolyzable groups comprise ethoxyl or methoxyl groups.

Suitable alkyl groups include methyl, ethyl and butyl.

Compounds suitable for use as the first organosilane of the present invention include: 3-aminopropyltrimethoxysilane, 3-aminopropylmethyldiethoxysilane, 3-mercaptopropyltrimethoxysilane, 3-mercaptomethylmethyldiethoxysilane, 3-mercaptopropylmethyldimethoxysilane, 3-methacrylopropyltrimethoxysilane, 3-methacrylopropylmethyldiethoxysilane, chloromethyltriethoxysilane, 3-chloropropylmethyldimethoxysilane, 3-glycioxypropyltrimethoxysilane, vinyl trimethoxysilane, vinyl triethoxysilane, allyltrimethoxysilane, allyl triethoxysilane, 3-isocyanatopropyltriethoxysilane.

The first organosilane is reacted with a second organosilane to form the coupling agent of the present invention.

Organosilanes which are suitable for use as the second organosilane of the present invention are those according to the structural formula:

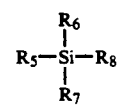

wherein:

$R_5$ is a reactive functional group, a hydrolyzable group or an alkyl group;
$R_6$ and $R_7$ are hydrolyzable groups; and
$R_8$ is a reactive functional group capable of forming a chemical bond with a metal substrate.

$R_5$ may be any of the reactive functional groups, hydrolyzable groups and alkyl groups described above in regard to the first organosilane. Preferably, $R_5$ comprises an alkoxyl or mercaptoalkyl group. Most preferably, $R_5$ is methoxyl, ethoxyl, mercaptoethyl or mercaptopropyl.

$R_6$ and $R_7$ may be any of the hydrolyzable groups described above in regard to the first organosilane. Preferably, $R_6$ and $R_7$ are methoxyl or ethoxyl.

$R_8$ may be any reactive functional group capable of forming a chemical bond with a metal substrate. For example $R_8$ may be an aminoalkyl (e.g. aminopropyl, aminobutyl) group, a mercaptoalkyl (e.g. mercaptomethyl, mercaptopropyl) group or a diphenylphosphinoalkyl (e.g. diphenylphosphinoethyl) group.

Compounds suitable for use as the second organosilane of the present invention include: 3-aminopropyltrimethoxysilane, 3-aminopropyldiethoxysilane, 3-mercaptopropyltrimethoxysilane, 3-mercaptomethylmethyldiethoxylsilane, 2-(diphenylphosphino) ethyltriethoxysilane. Prehydrolyzed 3-mercaptopropyl trimethoxysilane is particularly preferred as the second organosilane.

The $R_5$ group of the second organosilane and the $R_4$ groups of the first organosilane are chosen so that the $R_5$ group may be reacted with the $R_4$ group according to any conventional reaction known in the art of organosilicon chemistry under appropriate conventional reaction conditions to provide a coupling agent having a structural formula according to:

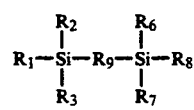

wherein:

$R_1$, $R_2$, $R_3$, $R_6$, $R_7$ and $R_8$ are defined as above, and
$R_9$ is a group formed by the reaction of the $R_4$ group on the first organosilane with the $R_5$ groups on the second organosilane. For example, in a preferred embodiment wherein $R_4$ and $R_5$ are each hydrolyzable groups, $R_9$ is an oxygen group. Similarly, $R_9$ may be alkylaminoalkyl if $R_4$ is haloalkyl and $R_5$ is aminoalkyl, $R_9$ may be alkylthioalkyl, if $R_4$ is alkenyl and $R_5$ is mercaptoalkyl, or $R_9$ may be alkyl, if $R_4$ is haloalkyl and $R_5$ is alkoxyl.

Coupling agents of the present invention include:

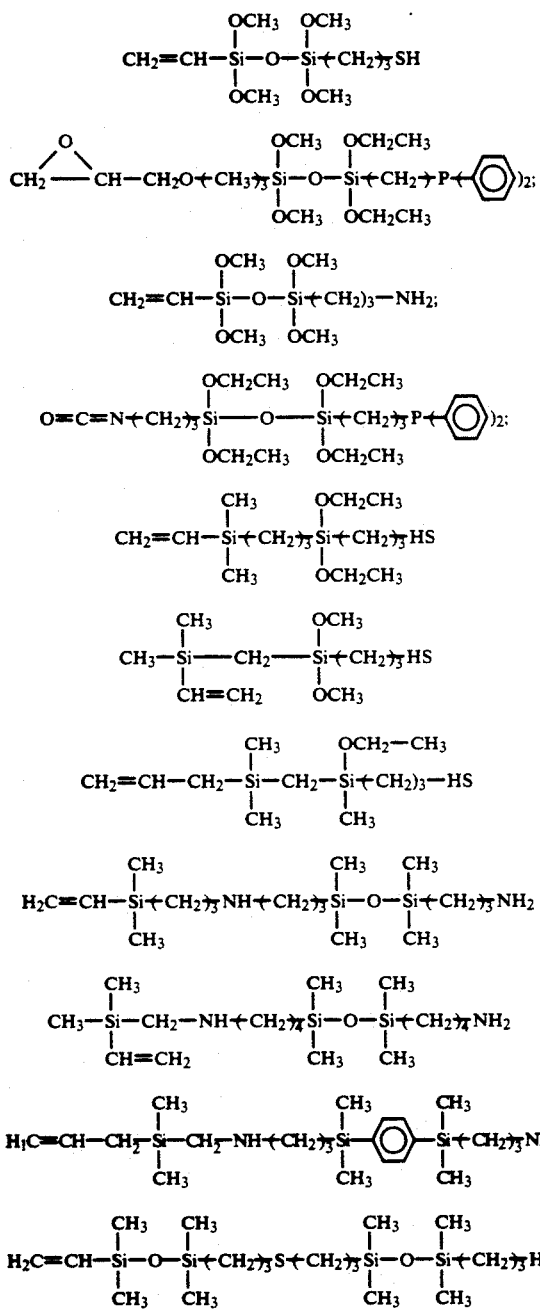

The etched surface of the substrate is contacted with the coupling agent of the present invention. Preferably, the coupling agent is dissolved in a volatile solvent to promote the formation of a uniform film of coupling agent on the surface of the substrate. Methylethylketone is preferred as the solvent. The coupling agent and substrate are subjected to conditions chosen to drive a reaction between the $R_1$ group on the coupling agent and the reactive groups on the etched surface toward completion to chemically bond the coupling agent to the surface of the substrate. The type of reaction is dependent upon the particular reactive group on the surface of the substrate and the particular $R_1$ group and may be any conventional reaction known in the art of organosilane chemistry conducted under appropriate reactive conditions. For example, a vinyl group on the coupling agent may be reacted with unsaturated groups on the surface of the substrate by a free radical reaction under reaction conditions wherein the substrate surface is contacted with a solution of the coupling agent and a free radical initiator, e.g. benzoylperoxide, in a suitable solvent, e.g. methylethylketone, and the substrate and solution are heated to drive the reaction forward.

Alternatively, the coupling agent of the present invention may be formed in situ. The surface of the substrate is contacted with the first organosilane and the $R_1$ group on the first organosilane is reacted with a reactive group on the surface of the substrate to form a silane modified surface having unreacted $R_4$ groups thereon. The silane modified surface is contacted with the second organosilane and the $R_5$ group on the second organosilane is reacted with the $R_4$ group on the first organosilane according to any of the reactions discussed above to form the coupling agent of the present invention in situ and bonded to the surface of the substrate, according to:

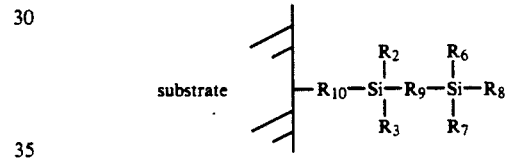

wherein:

$R_2$, $R_3$, $R_6$, $R_7$, $R_8$ and $R_9$ are defined as above, and, $R_{10}$ is a group formed by the reaction of the reactive group on the surface of the substrate and the $R_1$ group on the first organosilane.

For example, $R_{10}$ may be alkyl, alkylaminoalkyl or alkylmercaptoalkyl.

Alternatively, the surface may be contacted with the first and second organosilanes and subsequently subjected to appropriate reaction conditions to react the $R_1$ groups with the reactive groups on the surface of the substrate and to react the $R_4$ groups on the first organosilane with the $R_5$ groups on the second organosilane to form the coupling agent of the present invention in situ and bonded to the surface of the substrate.

In each of the above methods it is preferred that the surface is contacted with a solution of the first and second organosilane in a suitable solvent, e.g. methyethylketone, to promote formation of a uniform film of the first organosilane on the surface. Each of the above described methods provides a substantially monomolecular layer of the coupling agent of the present invention on the surface of the substrate wherein the $R_1$ groups on one end of the coupling agent is chemically bonded to the substrate, and the $R_8$ group on the other end of the coupling agent is available for chemically bonding the coupling agent to a metal substrate.

Since the pendant groups $R_2$, $R_3$, $R_6$ and $R_7$ on the coupling agent are hydrolyzable groups, the monomolecular layer may be crosslinked by hydrolyzing the hydrolyzable groups to form silanol groups and condensing neighboring silanol groups to form crosslinks between the coupling agent molecules of the layer.

A metallic layer is deposited over the surface of the substrate so that the $R_8$ groups on the coupling agent reacts with the metal layer to form a $R_{11}$ group and chemically bond the coupling agent with the metal layer as schematically illustrated in FIG. 2 and wherein the $R_{11}$ group may be the reaction product of any of the $R_8$ group described above with any suitable metal. For example the $R_{11}$ group may be $R_8$-Cu, $R_8$-Pd, or $R_8$-Au. The metallic layer may be deposited by conventional vacuum deposition or by conventional electroless deposition techniques. Preferably the metallic layer is deposited by electroless deposition. In a preferred electroless deposition process, a paladium (pd) catalyst is deposited on the surface of the substrate. The pd catalyst reacts with the organosilane coupling agent to form a chelation complex. A copper layer is electrolessly deposited over the chelated catalyst to metallize the substrate.

The coupling agents of the present invention provides a chemical linkage between the substrate and the metal layer.

EXAMPLE 1

A substrate material was made by the melt extrusion of PFA (Dupont TE-97645) with 6 wt % microglass filler (Johns-Manville 104E).

Samples of the substrate material were rinsed with hexane and allowed to dry.

The samples were then dipped into a container of sodium naphthalene etchant (Matheson Gas Polytech W) for one minute with slight agitation. The samples were removed from the etchant and rinsed in hot (80°-90° C.) distilled water. Following the water rinse, the samples were rinsed in acetone to remove the etchant residue.

A 1% solution of vinyl trimethoxy silane with 2% benzoyl peroxide and 0.4% distilled water in methyl ethylketone (MEK) was prepared and mixed for 90 minutes.

A 1% solution of 3-mercaptopropyl trimethoxy silane with 3.0% distilled water in MEK was prepared and mixed for 90 minutes.

The samples of substrate material were dipped in the vinyl silane solution for 20 seconds, removed from the solution and allowed to drain. The samples were then dipped in the mercapto silane solution for 15 seconds and removed. The samples were air dried and baked for 1 hr at 110° C. to react the vinyl groups with the substrate and to promote the condensation reaction between the two organosilanes to form the coupling agent of the present invention in situ and chemically bonded to the substrate.

Copper layers were deposited on the samples by electroless deposition.

The samples so prepared were subjected to 90° peel strength testing according to MIL-P-13949F both as prepared and following thermal aging (1 hour bake at 220° C.). The performance was compared to control samples prepared without the coupling agent of the present invention.

The samples prepared according to the present invention provided peel strengths ranging from about 13-15 pound/linear inch and exhibited no significant reduction in peel strength following the thermal aging.

The control samples exhibited a peel strength of about 7 pounds/linear inch, which dropped to about 3 pounds per linear inch after thermal aging.

EXAMPLE 2

A coupling agent of the present invention is made by forming a silicon-carbon bond using an organometallic reactant according to:

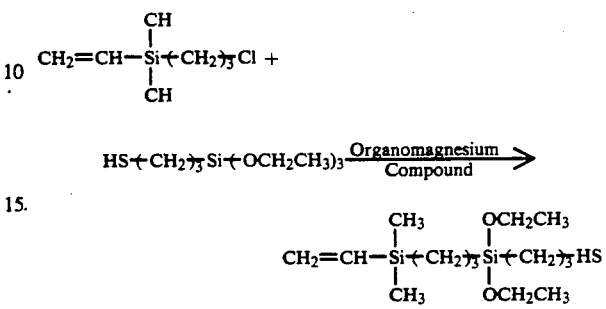

The following coupling agents are made in a similar manner:

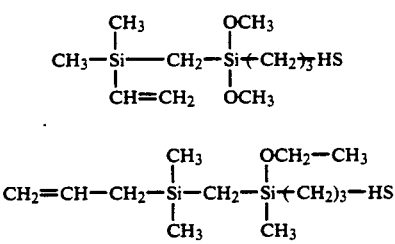

EXAMPLE 3

A coupling agent of the present invention is made by a nucleophilic substitution reaction of an alkyl halide with an diaminosilane according to:

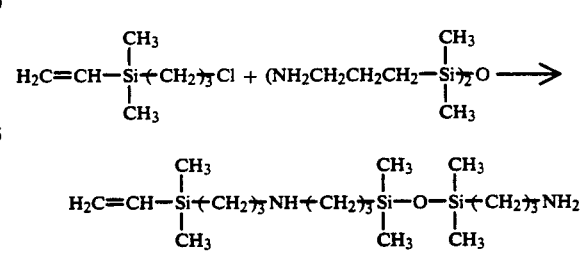

The following coupling agents are made in a similar manner:

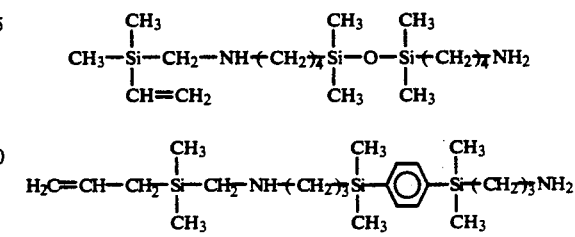

EXAMPLE 4

A coupling agent of the present invention is made according to the reaction:

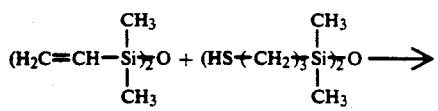
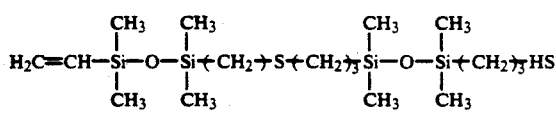

The coupling agent and method of the present invention provide improved adhesion between the metal layer and the polymeric layer of a metallized polymeric substrate.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A coupling agent for coupling a metal layer to a polymeric layer, said polymeric layer having first reactive functional groups formed thereon, said coupling agent having the structural formula:

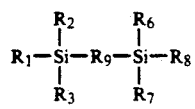

wherein:
- $R_1$ is a second reactive functional group capable of undergoing reaction with the first reactive functional group on the polymeric layer to form a chemical bond between the coupling agent and the polymeric layer and is selected from the group consisting of aminoalkyl, haloalkyl, mercaptoalkyl, carboxyalkyl, glycidoxyalkyl, alkenyl and isocyanatoalkyl;
- $R_2$, $R_3$, $R_6$ and $R_7$ are each selected from the group consisting of hydrolyzable groups and alkyl groups;
- $R_8$ is a third reactive functional group capable of undergoing reaction with the metal layer to form a chemical bond between the coupling agent and the metal layer and is selected from the group consisting of aminoalkyl, mercaptoalkyl and dimethylphosphinoalkyl; and
- $R_9$ is selected from the group consisting of oxygen, alkyl, alkylaminoalkyl and alkylthioaklyl.

2. The coupling agent of claim 1, wherein $R_2$, $R_3$, $R_6$ and $R_7$ are each independently hydroxyl, alkoxyl or halo.

3. The coupling agent of claim 1, wherein $R_1$ is glycidoxyalkyl, $R_2$, $R_3$, $R_6$ and $R_7$ are each alkoxyl, $R_8$ is aminoalkyl and $R_9$ is oxygen.

4. The coupling agent of claim 1, wherein $R_2$, $R_3$, $R_6$ and $R_7$ are each hydroxyl or alkoxyl.

5. The coupling agent of claim 1, wherein the coupling agent has the structural formula:

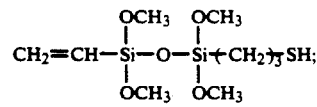
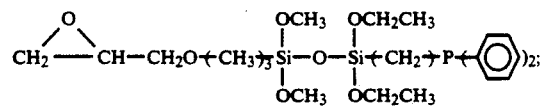
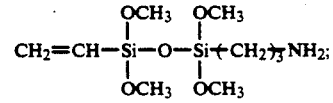
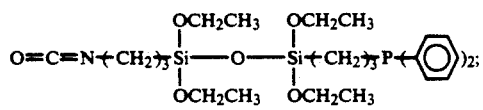
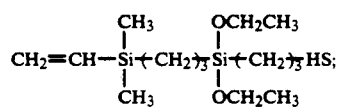
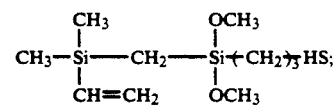
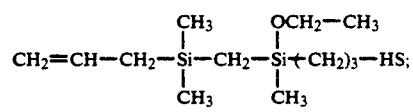
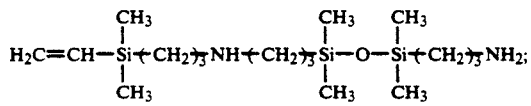
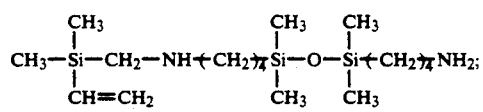
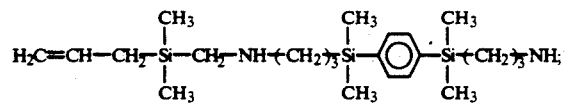

or

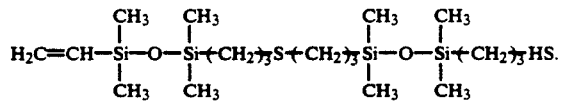

6. A coupling agent having the structural formula:

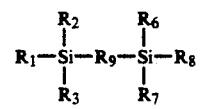

wherein $R_1$ is alkenyl, $R_2$, $R_3$, $R_6$ and $R_7$ are each alkoxy, $R_8$ is mercaptoalkyl and $R_9$ is oxygen.

* * * * *